(12) United States Patent
Arce Vera et al.

(10) Patent No.: US 9,259,404 B2
(45) Date of Patent: Feb. 16, 2016

(54) 4-OXO-2-PENTENOIC ACID AND BRAIN HEALTH

(71) Applicant: NESTEC S.A., Vevey (CH)

(72) Inventors: Francia Jacqueline Arce Vera, Lausanne (CH); Bertrand Bourqui, Murist (CH); Timo Buetler, Zurich (CH); Stephane Duboux, St-Prex (CH); Jane Durga, Miex (CH); Francis Foata, Lausanne (CH); Philippe Alexandre Guy, Lucens (CH); Nicolas Page, Lausanne (CH); Serge Andre Dominique Rezzi, Semsales (CH); Pierre Magistretti, Epalinges (CH); Evelyne Ruchti, Lausanne (CH); Sylvain Lengacher, Lausanne (CH); Igor Allaman, Lausanne (CH)

(73) Assignee: Nestec S.A., Vevey (CH)

( * ) Notice: Subject to any disclaimer, the term of this patent is extended or adjusted under 35 U.S.C. 154(b) by 5 days.

(21) Appl. No.: 14/389,082

(22) PCT Filed: Mar. 25, 2013

(86) PCT No.: PCT/EP2013/056253
§ 371 (c)(1),
(2) Date: Sep. 29, 2014

(87) PCT Pub. No.: WO2013/144077
PCT Pub. Date: Oct. 3, 2013

(65) Prior Publication Data
US 2015/0105464 A1    Apr. 16, 2015

(30) Foreign Application Priority Data
Mar. 30, 2012 (EP) .................... 12162358

(51) Int. Cl.
*A61K 31/19* (2006.01)
*A23L 1/30* (2006.01)
*C12N 1/20* (2006.01)
*C12P 7/40* (2006.01)
*A61K 35/74* (2015.01)

(52) U.S. Cl.
CPC . *A61K 31/19* (2013.01); *A23L 1/30* (2013.01); *A61K 35/74* (2013.01); *C12N 1/20* (2013.01); *C12P 7/40* (2013.01); *A23V 2002/00* (2013.01); *A23Y 2300/29* (2013.01)

(58) Field of Classification Search
CPC ..................................................... A61K 31/19
See application file for complete search history.

(56) References Cited

U.S. PATENT DOCUMENTS

| | | | | |
|---|---|---|---|---|
| 8,022,246 B2 * | 9/2011 | Lipton | .................... | C07C 62/32 |
| | | | | 562/403 |
| 2005/0261371 A1 | 11/2005 | Ohuchida et al. | | |
| 2009/0042980 A1 | 2/2009 | Lipton et al. | | |
| 2010/0022461 A1 * | 1/2010 | Cho | ....................... | C07C 43/184 |
| | | | | 514/23 |

FOREIGN PATENT DOCUMENTS

WO      9313076      7/1993

OTHER PUBLICATIONS

Vargas MR, Johnson DA, Sirkis DW, Messing A, Johnson JA. Nrf2 activation in astrocytes protects against neurodegeneration in mouse models of familial amyotrophic lateral sclerosis. J Neurosci. Dec. 10, 2008;28(50)13574-81.*
Kakinuma et al. "Structure-Activity Relationship and Design of an Antimutagen against the UV-Induced Mutation of *Escherichia coli*" Agric. Biol. Chem., vol. 50, 1986, pp. 625-631.

* cited by examiner

*Primary Examiner* — Paul Zarek
(74) *Attorney, Agent, or Firm* — K&L Gates LLP

(57) ABSTRACT

The present invention relates generally to compositions with a health benefit. In particular, the invention relates to the field of brain health, for example brain protection, maintenance of cognitive function, prevention of cognitive decline and prevention of cognitive disorders. A subject matter of the invention is a composition comprising 4-oxo-2-pentenoic acid for use in the treatment or prevention of cognitive decline.

12 Claims, 5 Drawing Sheets

4-OXO-2-PENTENOIC ACID AND BRAIN HEALTH

CROSS REFERENCE TO RELATED APPLICATIONS

Figure 1:
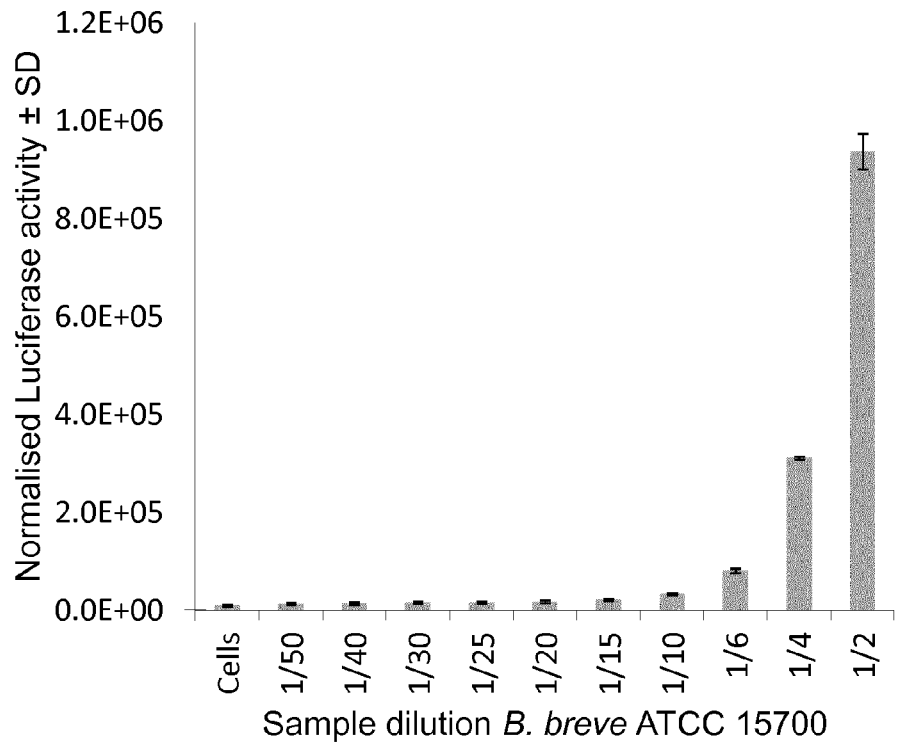

The present application is a National Stage of International Application No. PCT/EP2013/056253, filed on Mar. 25, 2013, which claims priority to European Patent Application No. 12162358.1, filed Mar. 30, 2012, the entire contents of which are being incorporated herein by reference.

The present invention relates generally to compositions with a health benefit. In particular, the invention relates to the field of brain health, for example brain protection, maintenance of cognitive function, prevention of cognitive decline and prevention of cognitive disorders. A subject matter of the invention is a composition comprising 4-oxo-2-pentenoic acid for use in the treatment or prevention of cognitive decline.

In almost every country the proportion of people aged over 60 is growing faster than any other age group, which is at least in part due to a longer life expectancy. This ageing of the population can be seen as a success story for increasing health awareness as well as for improved availability and performance of public health care. According to the United Nations Population Division, the world's population of people older than 60 is presently just under 900 million. By 2050, the population over 60 is forecast to reach 2.4 billion. However, ageing increases the risk of developing a number of diseases and so it is an important aim of our society today to allow the population to age in good health. Central to the quality of life, in particular for the ageing population, is proper cognitive performance and its maintenance.

Most common mental disorders affect cognitive functions, mainly memory processing, perception and problem solving. The most direct cognitive disorders are amnesia, dementia and delirium. Alzheimer's disease is one form of dementia. Several age related disorders may be treated or prevented by appropriate nutrition. However, very little is known about nutritional measures that can be taken to prevent cognitive disorders. There is hence a great need for compositions that may be used to secure proper cognitive function. In particular there is a need to identify compositions which can be used in the treatment or prevention of cognitive decline.

Consequently, it was the object of the present invention to improve the state of the art and in particular to provide a composition that can be used to maintain cognitive function and to prevent or treat cognitive decline and/or cognitive disorders.

The inventors were surprised to see that the object of the present invention could be achieved by the subject matter of the independent claims. The dependent claims further develop the idea of the present invention.

Accordingly, the present invention provides a composition comprising 4-oxo-2-pentenoic acid for use in the treatment or prevention of cognitive decline. The composition may be not to be used as a pharmaceutical.

The present invention also provides the use of 4-oxo-2-pentenoic acid in the preparation of a composition for the treatment or prevention of cognitive decline.

"Treatment" within the scope of the present invention refers to reduction, inhibition, alleviation or amelioration. "Cognitive decline" within the scope of the present invention refers to deterioration in cognitive function. Cognitive decline may be caused by, for example, changes in brain function, particularly brain aging, or damage from disease. 4-oxo-2-pentenoic acid has the CAS number 4743-82-2 and the following formula

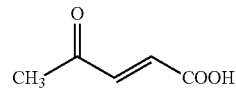

Increased oxidative stress contributes to the decline in cognitive performance during normal aging and in neurodegenerative conditions such as Alzheimer's disease. Oxidative stress results from the impairment of human cells in controlling cell damages due to reactive oxygen species (free radicals and peroxides) or in detoxifying reactive intermediates. Production of peroxides and free radicals leads to damage of cell components, including proteins, lipids and DNA. It is however noteworthy that under specific conditions, reactive oxygen species can be beneficial, as they are used by the immune system as a way to kill invading pathogens.

Undesired effects of oxidative stress have been found to be controlled by anti-oxidants. Nuclear factor (erythroid-derived 2)-like 2, also called Nrf2 is a master regulator of the antioxidant response. The inventors were surprised to find that 4-oxo-2-pentenoic acid activates Nrf2. The activation of Nrf2 is known to play a critical role in protecting neurons in many acute models of neuronal damage (Vargas M. R. et al., Journal of Neuroscience, 28(50), 13574-13581, 2008).

The transcription factor Nrf2 resides in the cytosol and is bound to an inhibitor Keap1. When bound to Keap1, Nrf2 is also rapidly degraded by the proteasome hence its low basal concentration. Upon activation by stressors, for example nitric oxide, growth factors or heavy metals, Nrf2 is released from Keap1. Nrf2 concentration increases and it translocates into the nucleus. Nrf2 then binds to the antioxidant-response element (ARE) that is present in the promoter region of genes encoding many antioxidant enzymes (Kensler T W et al., Annu Rev Pharmacol Toxicol 2007; 47:89-116).

Activation of Nrf2 by food compounds has been described. Polyphenols such as curcumin (Balogun E et al., Biochem J 2003 May 1; 371(Pt 3):887-95.), resveratrol (Chen C Y et al., Biochem Biophys Res Commun 2005 Jun. 17; 331(4):993-1000), sulphoraphane (F. Elbarbry et al., Journal of Medical Plants Research, 5, 473-484, (2011)) and quercitin (Tanigawa S et al., Free Radic Biol Med 2007 Jun. 1; 42(11):1690-703) isolated from turmeric rhizome, grapes, broccoli and apples, respectively have been reported to activate Nrf2. US2009/0042980 for example describes compositions which comprise a neuroprotective amount of an electrophilic compound, wherein the electrophilic compound causes dissociation of Nrf2 from a Keap1/Nrf2 complex in a cell of a mammal. An example of such an electrophilic compound described in the patent is curcumin. However, the absorption and bioavailability of these compounds in the body remains to be determined and so there remains a need to identify further compounds and compositions which can be used to control the undesired effects of oxidative stress. The very low aqueous solubility of curcumin, resveratrol, sulphoraphane and quercitin affects their bio-availability. 4-oxo-2-pentenoic acid, by contrast, has good aqueous solubility.

Oxidative stress is a process that has been associated with neurodegeneration in several pathologies (A. Reynolds et al., Int. Rev. Neurobiol., 82, 297-325 (2007)). The inventors investigated whether 4-oxo-2-pentenoic acid protects neurons from oxidative stress. Using a co-culture model of neurons and astrocytes they found that 4-oxo-2-pentenoic acid protects neuronal cells against oxidative stress induced by hydrogen peroxide.

The inventors were also surprised to find that 4-oxo-2-pentenoic acid was obtainable from some heat treated bacterial strains. For example, bacterial preparations of *Bifidobacterium breve* CNCM I-3865 and *Bifidobacterium breve* ATCC 15700™ both yielded 4-oxo-2-pentenoic acid when heated for 6 hours at 90° C. 4-oxo-2-pentenoic acid was found to be in the soluble fraction after centrifuging and filtering the heat treated bacterial preparations.

*Bifidobacterium breve* CNCM I-3865 was deposited with the COLLECTION NATIONALE DE CULTURES DE MICROORGANISMES (CNCM), INSTITUT PASTEUR, 25 rue du Docteur Roux, F-75724 PARIS Cedex 15, France, on Nov. 15, 2007.

*Bifidobacterium breve* ATCC 15700™ can be obtained commercially, e.g., from the American type Culture Collection (ATCC), Manassas, Va., USA, under the trademark ATCC 15700.

Consequently the present invention relates in part to a composition comprising 4-oxo-2-pentenoic acid for use in the treatment or prevention of cognitive decline wherein the composition is not to be used as a pharmaceutical. A pharmaceutical is a drug or medicine that is prepared or dispensed in pharmacies and used in medical treatment (<URL: www.thefreedictionary.com/pharmaceutical/> [retrieved on 17 Jul. 2012]). The composition of the current invention may be for use in the treatment or prevention of memory loss, in particular short term memory loss. "Memory loss" within the scope of the present invention refers to a reduction in the ability to store, retain or recall information including past experiences, knowledge and thoughts. "Short term memory" within the scope of the present invention refers to the storage, retention and recall of information memorized up to one week before. Any type of memory loss can be a distressing and frightening experience which can severely affect people's lives. Short term memory loss in particular can make coping with everyday life very difficult and so a composition capable of treating memory loss is advantageous.

A composition of the present invention may be for use in the treatment or prevention of loss of learning capability. "Loss of learning capability" within the scope of the present invention refers to a reduction in the ability to acquire new knowledge or skills, or a reduction in the rate at which such knowledge or skills can be acquired. Loss of learning capability can prevent sufferers adapting to changes in their environment such as new accommodation. The increasingly complex nature of household items such as central heating timers, televisions or telephones can also create real hardship for those with a reduced capability for learning.

In the present invention the 4-oxo-2-pentenoic acid may be obtainable, for example obtained, from natural sources. Many people are concerned about the safety of materials industrially synthesised from chemical feedstock, especially when these materials are to be ingested and prefer materials obtained from natural sources.

Surprisingly, the inventors found that some strains of bacteria provide a natural source of 4-oxo-2-pentenoic acid. In particular, the inventors have found that 4-oxo-2-pentenoic acid can be obtained from *Bifidobacterium breve* CNCM I-3865 or *Bifidobacterium breve* ATCC 15700™ (the type strain for *Bifidobacterium breve*). It is particularly advantageous to use bacteria as a source of 4-oxo-2-pentenoic acid as the production of large quantities of 4-oxo-2-pentenoic acid is feasible, for example by using bioreactors. Accordingly, in the present invention the 4-oxo-2-pentenoic acid may be obtainable, for example obtained, from *Bifidobacterium breve* CNCM I-3865 or *Bifidobacterium breve* ATCC 15700™.

The bacteria may be heat treated at about 60-180° C., preferably at about 80-160° C., for example at about 110-150° C. in commercial production processes. The inventors found that heat treatment at these temperatures provided a satisfactory yield of 4-oxo-2-pentenoic acid within an acceptable time. Without wishing to be bound by theory it is understood that increasing the temperature of heat treatment increases the rate of formation of 4-oxo-2-pentenoic acid but also increases the rate of its degradation. Accordingly these temperatures give a good balance between the rate of formation of 4-oxo-2-pentenoic acid and its degradation.

Typical compositions comprising 4-oxo-2-pentenoic acid may comprise 4-oxo-2-pentenoic acid in an amount of at least 1 mg/kg of the composition. Generally, it is preferred if the composition comprises 4-oxo-2-pentenoic acid in an amount of at least 10 mg/kg of the composition, for example between 50 mg and 50 g per kg of the composition.

The optimum amount of 4-oxo-2-pentenoic acid to be administered can be easily determined by skilled artisans.

In therapeutic applications, compositions are administered in an amount sufficient to at least partially cure or arrest the symptoms of the disorder and/or its complications. An amount adequate to accomplish this is defined as "a therapeutic effective dose". Amounts effective for this purpose will depend on a number of factors known to those of skill in the art such as the severity of the disorder and the weight and general state of the patient. In prophylactic applications, compositions according to the invention are administered to a patient susceptible to or otherwise at risk of a particular disorder in an amount that is sufficient to at least partially reduce the risk of developing a disorder. Such an amount is defined to be "a prophylactic effective dose". Again, the precise amounts depend on a number of patient specific factors such as the patient's state of health and weight.

4-oxo-2-pentenoic acid may be administered in the framework of the present invention in a therapeutic effective dose and/or in a prophylactic effective dose. A composition of the present invention may be administered in a daily dose corresponding to between 2 µg and 20 mg of 4-oxo-2-pentenoic acid per kg of body weight, preferably between 20 µg and 2 mg of 4-oxo-2-pentenoic acid per kg of body weight, for example between 40 µg and 1 mg of 4-oxo-2-pentenoic acid per kg of body weight.

Cognitive decline can affect pets as well as humans. Both, healthily aging or geriatric pets, can exhibit various behavioural disorders. For example, aging pet dogs may not respond to their name or familiar commands, may get lost or confused even in familiar surroundings, may no longer greet or respond to their owners or visitors, may exhibit diminished daytime activity, may walk in circles, may shun affection, and may lose bladder or bowel control.

It is therefore an advantage to provide a composition to be administered to humans or pets. In the case of companion animals such therapies improve the animal's overall quality of life, improve owner satisfaction and improve the bond between the owner and companion animal. The composition of the present invention may be administered to humans or pets.

4-oxo-2-pentenoic acid and the composition described in the present invention may be administered to adults, in particular to the elderly. A subject is considered adult if they are of relatively mature age. Typically subjects are considered adult when they are sexually mature and capable of reproduction.

A subject is considered as "elderly" if they have surpassed the first two thirds of their average expected lifespan in their country of origin, preferably if they have surpassed the first three quarters of the average expected lifespan in their country of origin, more preferably if they have surpassed the first four fifths of the average expected lifespan in their country of origin. For example, a human male born in the UK in 2010 has a life expectancy at birth of 78 years according to the UK Office of National Statistics, therefore they would be considered elderly at ages over 52 years, preferably over 58 years 6 months and more preferably over 62 years 5 months.

For example, the composition may be to be administered to people at the age of at least 45, at least 60 or at least 75.

For pets the species and breed should be taken into account. For example a Yorkshire Terrier dog has a life expectancy of about 12 years (E. J. Taylor et al., Proceedings of the Nutrition Society, 54, 645-656 (1995)) and so would be considered elderly at ages over 8 years, preferably over 9 years and more preferably over 9 years 7 months.

The nature of the composition is not particularly limited. It may be a composition for oral or enteral administration. The composition may be for example selected from the group consisting of a food composition, a food additive, a nutraceutical, a drink, a nutritional formulation, a tube feeding formulation, a powdered composition to be reconstituted in milk or water, and a pet food composition.

The composition may be a food composition. Food compositions according to the present invention are diverse in character, for example: milk, yogurt, cheese, fermented milks, milk-based fermented products, ice-creams, cereal-based products or fermented cereal-based products, milk-based powders, chilled or shelf stable beverages, confectionery, animal feed, in particular for domestic animals.

The food composition may also further comprise a protein source, a carbohydrate source, a lipid source, a mineral source and/or a vitamin source. The presence of proteins, carbohydrates, lipids, minerals and/or vitamins may have several advantages. These compounds generally contribute to the taste and mouthfeel of the final product. They also provide the body with nutrients that it may need urgently when it is affected by cognitive disorders. They also allow formulating the composition of the present invention as a complete nutritional formula, so that no additional nutrition is needed.

Compounds soluble in water have the advantage of being conveniently administered in a number of ways, including orally as solutions, or in capsules or tablets. The composition comprising 4-oxo-2-pentenoic acid may be water-based, for example the composition may comprise 4-oxo-2-pentenoic acid dissolved in water.

A composition comprising 4-oxo-2-pentenoic acid may be a nutraceutical composition. Within the scope of the present invention the term nutraceutical refers to a food stuff, as a fortified food, oral supplement or dietary supplement, that provides a health benefit.

Those skilled in the art will understand that they can freely combine all features of the present invention disclosed herein. In particular, features described for different embodiments of the present invention may be combined. Further advantages and features of the present invention are apparent from the following figures and non-limiting examples.

FIG. 1 shows normalized luciferase activities of crude preparations (OD 50, heated for 6 hours at 90° C.) of *Bifidobacterium breve* ATCC 15700™. The results are expressed on the y-axis as a mean±SD of technical triplicates. The x-axis values are the final dilutions of the sample.

Figure 2:
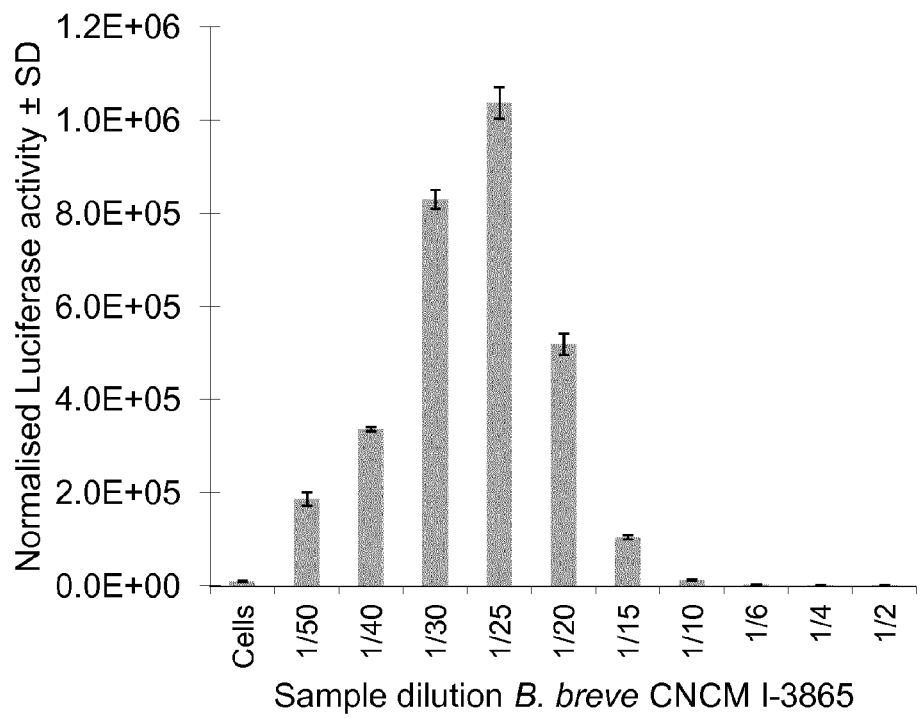

FIG. 2 shows normalized luciferase activities of crude preparations (OD 50, heated for 6 hours at 90° C.) of *Bifidobacterium breve* CNCM I-3865. The results are expressed on the y-axis as a mean±SD of technical triplicates. The x-axis values are the final dilutions of the sample.

Figure 3:
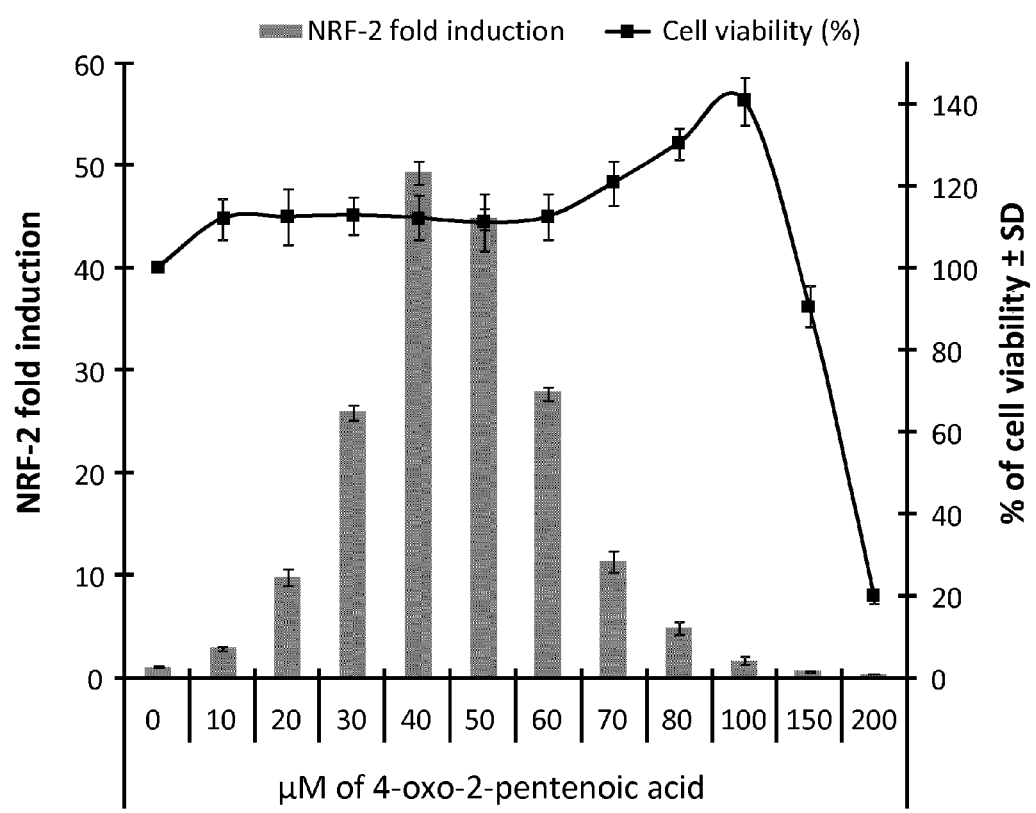

FIG. 3 shows Nrf2 induction-fold (bars) and percentage of cell viability (lines) of AREC32 cells incubated with of a dose range of 4-oxo-2-pentenoic acid from 0 to 200 µM. The Nrf2 fold inductions are ratios between the luciferase activity (RLU) of the AREC32 cells in the presence of 4-oxo-2-pentenoic acid and the basal luciferase activity of the unexposed cells. The cell viability, measured by ATP quantification, is expressed as relative percentages of control (untreated) cells. The results are expressed as means of technical triplicates±SD and are representative of four independent experiments.

Figure 4:
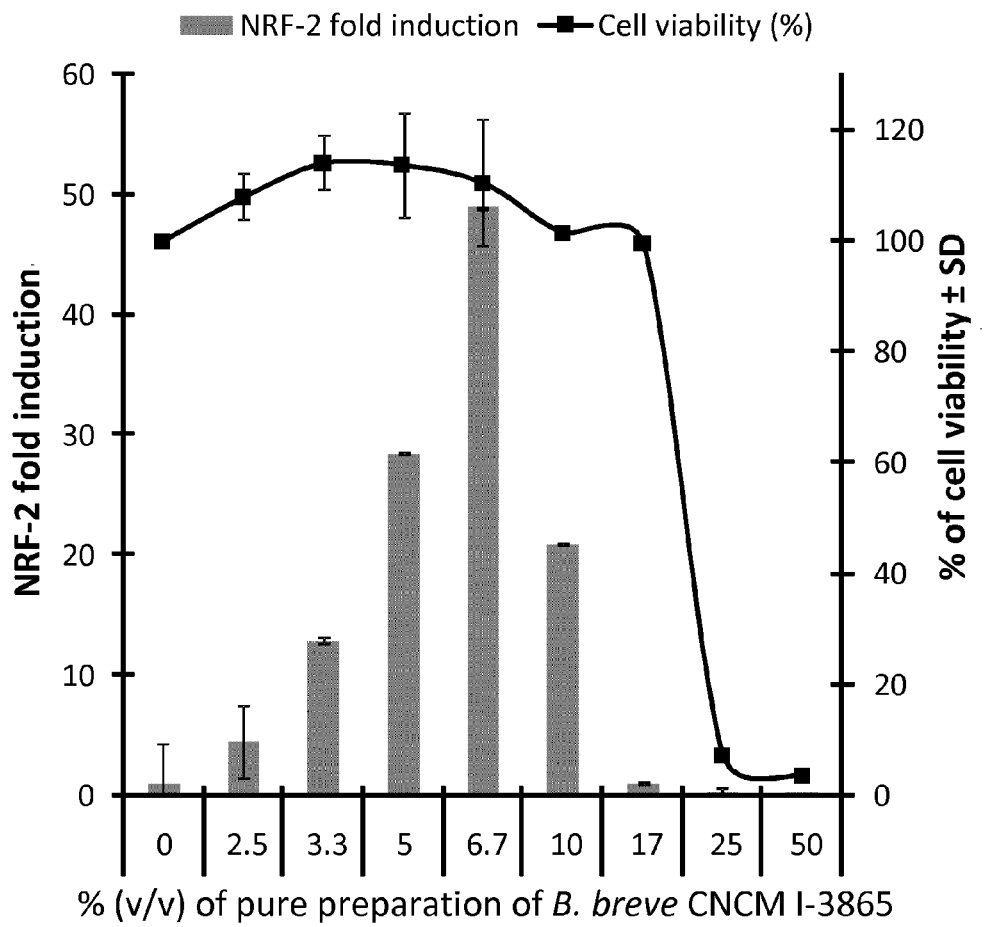

FIG. 4 shows Nrf2 induction-fold (bars) and percentage of cell viability (lines) of AREc32 cells incubated with of a dose range of a "pure preparation" of *Bifidobacterium breve* CNCM I-3865 from 2.5 to 50% v/v. Other details as for FIG. 3.

Figure 5:
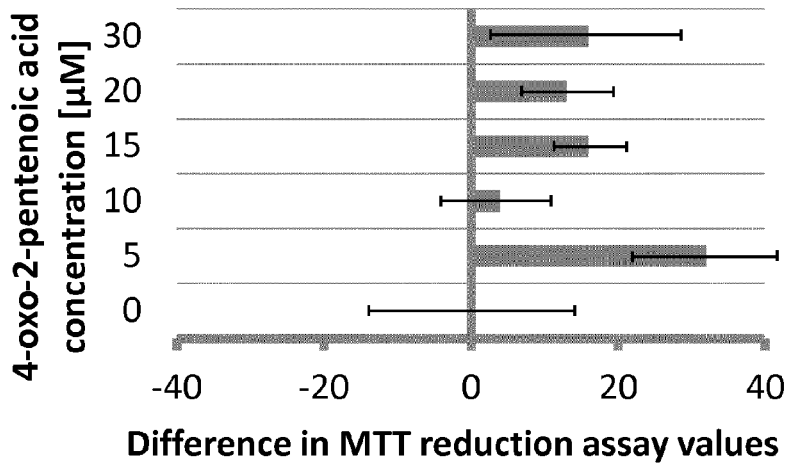

FIG. 5 shows the effect of 48 hour stimulation with 4-oxo-2-pentenoic acid at different concentrations (5 µM to 30 µM) on neuron astrocyte co-cultures with neurodegeneration induced by hydrogen peroxide (100 µM). Each concentration tested in triplicate in three separate experiments. Error bars are SEM.

Figure 6:
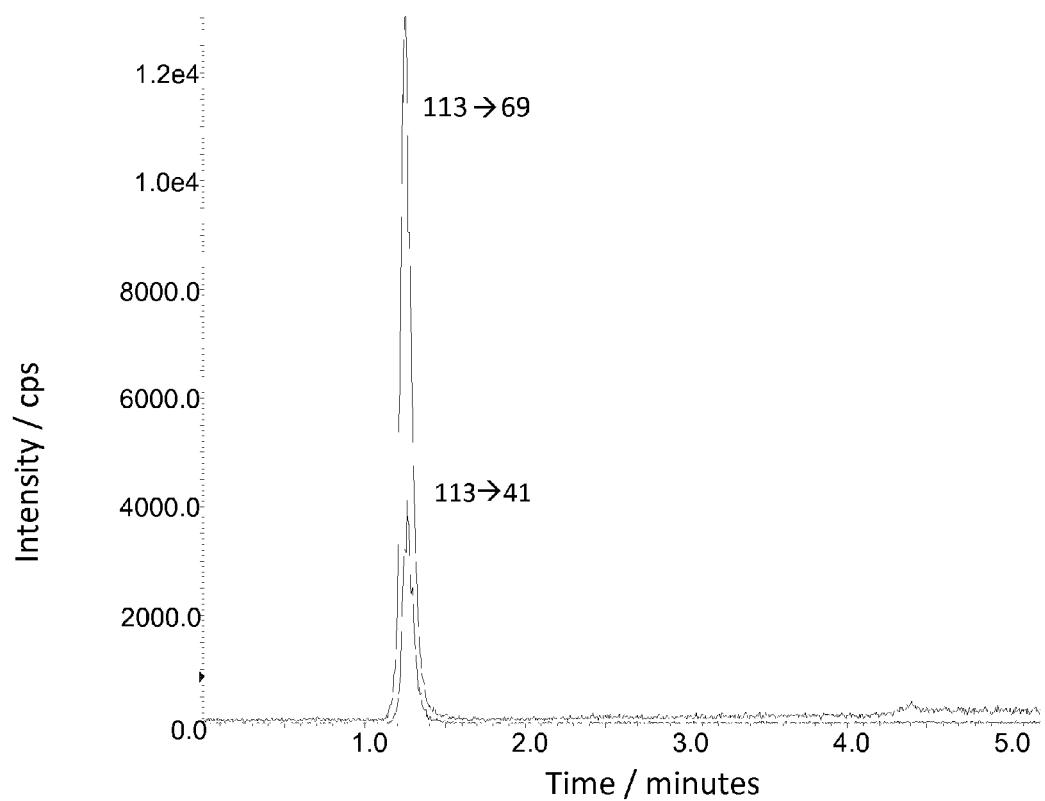

FIG. 6 shows a typical chromatogram of a 4-oxo-2-pentenoic acid standard dissolved in water. The higher SRM is associated to the transition reaction of m/z 113→69, while the lower SRM corresponds to transition reaction of m/z 113→41. The retention time is expressed in minutes (x-axis). Signal intensity (y-axis) is expressed in Cps.

Figure 7:
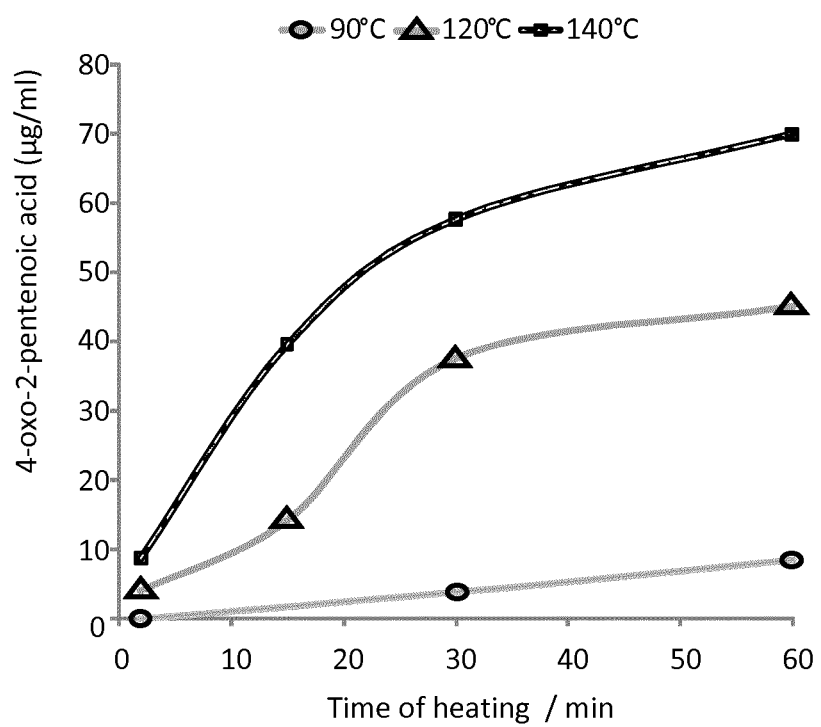

FIG. 7 shows 4-oxo-2-pentenoic acid quantification using HPLC-ESI-MS/MS of crude preparations of *Bifidobacterium breve* CNCM I-3865 (OD 40) heated for 2, 15, 30, and 60 minutes at 90° C. (indicated by circles ○), 120° C. (indicated by triangles Δ) and 140° C. (indicated by squares □).

EXAMPLE 1

Nrf2 Activation by 4-oxo-2-pentenoic Acid and Bacterial Fractions

Nrf2 Reporter Assay:

Activation of Nrf2 was measured using an Nrf2 reporter assay. This assay is based on the AREc32 cell line, from CRX biosciences (Dundee, Scotland), a stably transfected MCF7 (breast adenocarcinoma) cell line that contains a luciferase gene construct under the control of the ARE. Luciferase is an enzyme which digests luciferin and produces fluorescence. Anti-oxidative molecules such as Tert-butylhydroquinone (TBHQ) induce luciferase transcription via the activation of Nrf2 that binds to ARE. Luciferase activity is determined using a luciferase kit form Promega (Madison, Wis.). The luciferase activity is proportional to the activation of Nrf2.

Nrf2 Activation by Bacterial Fractions:

Three bacterial strains were used to investigate activation of Nrf2 by microorganisms: *Bifidobacterium breve* CNCM I-3865 (NCC2950), *Bifidobacterium breve* CNCM I-3914 (NCC466) and *Bifidobacterium breve* ATCC 15700™ (NCC2791). *Bifidobacterium breve* CNCM I-3914 was deposited with the COLLECTION NATIONALE DE CULTURES DE MICROORGANISMES (CNCM), INSTITUT PASTEUR, 25 rue du Docteur Roux, F-75724 PARIS Cedex 15, France, on Feb. 5, 2008.

For each strain, 10 ml of MRS agar with 0.05% cystein was inoculated with 20 µl of glycerol stock and incubated overnight at 37° C. in anaerobic condition to form pre-cultures.

Further cultures were then made by inoculating 10 ml of MRS with 0.05% cystein with the pre-cultures (final $OD_{600}$ adjusted at 0.1). The cultures were incubated for 16 hours at 37° C. in anaerobic conditions to form the P2 cultures. 200 ml of MRS with 0.05% cystein was inoculated with the P2 cultures (final $OD_{600}$ adjusted at 0.1) and the bottles were incubated for 16 hours at 37° C. in anaerobic conditions.

The $OD_{600}$ was measured, the cultures were centrifuged at 3300 g for 10 min and the bacterial pellets were washed two times with cold 1×PBS (phosphate buffered saline) and normalized to OD 50 with 1×PBS.

Bacterial fractions were obtained in two ways for each bacterial strain; a "crude preparation" and a "pure preparation".

The bacterial "crude preparations" were obtained as follows. 5 ml of the OD 50 bacterial preparations were heated for 6 hours at 90° C. in a heating block (Dri-Block DB-3 heating block from Techne, Staffordshire, United Kingdom). The heated bacterial preparations were centrifuged at 3300 g for 10 min at +4° C. and the supernatants were filtered using 0.22 µm syringe filters and stored at +4° C. until further analyses.

The bacterial "pure preparations" were obtained as follows. 5 ml of the OD 50 bacterial preparations were centrifuged at 3300 g for 10 min at +4° C. and the bacterial pellets were re-suspended with 5 ml of water. The bacterial cells were disrupted using mini bead beat (MBB) apparatus in a cold room (six cycles of 90 sec at maximum speed with 10 min of pause between each cycle). The disrupted cells were centrifuged for 1 h at 3300 g at +4° C. and the pellet was re-suspended with 5 ml of 1×PBS and heated for 6 hours at 90° C. in a heating block. The heated preparations were centrifuged for 10 min at 3300 g at +4° C. The supernatants were filtered using 0.22 µm syringe filters and stored at +4° C. until further analyses.

The live bacteria counts of the "OD 50 suspensions" were determined by plating using a spotting method, and the dry weights determined using a halogen moisture analyzer (Metler-Toledo, Greifensee, Switzerland) with the following settings: drying temperature 160° C. with step-drying activated.

To determine the Nrf2 activation the samples were tested on AREC32 cells (seeded in 96 well plates) using 10 independent dilutions (1/2, 1/4, 1/6, 1/10, 1/15, 1/20, 1/25, 1/30, 1/40 and 1/50) and incubated for 24 hours at 37° C. in a 5% $CO_2$/air incubator. The luciferase activity and the cell viability (ATP measurements) were determined using the Luciferase and Cell Titer-Glo kits from Promega.

For each run the luciferase activities, measured in Relative Light Units (RLU), of all the wells were normalized with the mean of the luciferase activity of the cells only of all the plates. Among all the samples tested the normalization procedure was found not to affect the data and this observation permits the comparison of samples measured in different runs.

For each sample the Nrf2 activation was calculated as follows:

1) The Nrf2 fold induction:

$$Nrf2 \text{ fold induction} = \frac{\text{Normalized luciferase activity of the sample}}{\text{Normalized luciferase activity of the cells}}$$

The Nrf2 fold induction is very useful for screening purposes. However the Nrf2 fold induction is a qualitative measurement only, because this calculation does not take into account the sample dilution.

2) The luciferase content per sample:

$$\begin{pmatrix} \text{Luciferase} \\ \text{content} \\ \text{per sample} \end{pmatrix} = \begin{pmatrix} \text{Normalized luciferase} \\ \text{activity of the sample} \\ \text{dilution giving the highest} \\ Nrf2 \text{ fold induction} \end{pmatrix} \times \begin{pmatrix} \text{Dilution factor} \\ \text{giving the highest} \\ Nrf2 \text{ fold induction} \end{pmatrix}$$

The "luciferase content per sample" also reflects Nrf2 activation but can differentiate two samples activating Nrf2 at similar Nrf2 fold inductions since this calculation takes into account the sample dilution.

The luciferase content per sample allows a semi quantification of the Nrf2 activation by reflecting the amount of the Nrf2 activating molecule.

TABLE A

Normalized luciferase activities and calculation of "luciferase content per sample" for crude preparations (OD 50, heated for 6 hours at 90° C.) of *Bifidobacterium breve* ATCC 15700 ™

*Bifidobacterium breve* ATCC 15700

Normalized luciferase content of the cells = 9583

| | Sample dilution | | | | | | | | | |
|---|---|---|---|---|---|---|---|---|---|---|
| | 1/2 | 1/4 | 1/6 | 1/10 | 1/15 | 1/20 | 1/25 | 1/30 | 1/40 | 1/50 |
| Normalized luciferase | 9.37E5 | 3.11E5 | 8.02E4 | 3.28E4 | 2.15E4 | 1.72E4 | 1.54E4 | 1.52E4 | 1.41E4 | 1.32E4 |
| Dilution factor | 2 | 4 | 6 | 10 | 15 | 20 | 25 | 30 | 40 | 50 |
| Nrf2 fold induction | 97.8 | 32.5 | 8.4 | 3.4 | 2.2 | 1.8 | 1.6 | 1.6 | 1.5 | 1.4 |

Luciferase content per sample = 9.37E5 × 2 = 1.87E6

(The scientific notation 9.4E5 is equivalent to $9.4 \times 10^5$)

TABLE B

Normalized luciferase activities and calculation of "luciferase content per sample" for crude preparations (OD 50, heated for 6 hours at 90° C.) of *Bifidobacterium breve* CNCM I-3865
*Bifidobacterium breve* CNCM I-3865
Normalized luciferase content of the cells = 9583

| | Sample dilution | | | | | | | | | |
|---|---|---|---|---|---|---|---|---|---|---|
| | 1/2 | 1/4 | 1/6 | 1/10 | 1/15 | 1/20 | 1/25 | 1/30 | 1/40 | 1/50 |
| Normalized luciferase | 1.16E3 | 1.46E3 | 2.62E3 | 1.24E4 | 1.05E6 | 5.19E5 | 1.04E6 | 8.30E5 | 3.37E5 | 1.87E5 |
| Dilution factor | 2 | 4 | 6 | 10 | 15 | 20 | 25 | 30 | 40 | 50 |
| Nrf2 fold induction | 0.1 | 0.2 | 0.3 | 1.3 | 10.9 | 54.1 | 108.3 | 93.4 | 35.1 | 19.5 |

Luciferase content per sample = 1.04E+06 × 25 = 2.60E+07

As illustrated in tables A and B, both crude preparations of *B. breve* ATCC 15700™ and *B. breve* CNCM I-3865 have similar maximum Nrf2 induction but different luciferase content/sample values. The difference in luciferase content per sample values reflect their corresponding Nrf2 activation patterns (see FIGS. 1 and 2).

In contrast *Bifidobacterium breve* CNCM I-3914 did not significantly activate Nrf2, see comparison table C.

TABLE C

Comparison of results from the three different *Bifidobacterium breve* strains - crude preparation.

| B. breve strain code | cfu/ml | Dry weight (mg/ml) | Normalized luciferase activity | Dilution factor giving the highest Nrf2 fold induction | Nrf2 fold induction | Luciferase content per sample |
|---|---|---|---|---|---|---|
| CNCM I-3865 | 2.5E10 | 24.8 | 1.04E6 | 25 | 108.3 | 2.60E7 |
| ATCC 15700 | 1.7E10 | 23.2 | 9.37E5 | 2 | 97.8 | 1.87E6 |
| CNCM I-3914 | 1.8E10 | 24.1 | 3.06E4 | 2 | 3.2 | 6.12E4 |

TABLE D

Comparison of results from the three different *Bifidobacterium breve* strains - pure preparation.

| B. breve strain code | cfu/ml | Dry weight (mg/ml) | Normalized luciferase activity | Dilution factor giving the highest Nrf2 fold induction | Nrf2 fold induction | Luciferase content per sample |
|---|---|---|---|---|---|---|
| CNCM I-3865 | 2.5E10 | 24.8 | 8.00E5 | 40 | 106 | 3.20E7 |
| ATCC 15700 | 1.7E10 | 23.2 | 6.55E5 | 6 | 68.4 | 3.93E6 |
| CNCM I-3914 | 1.8E10 | 24.1 | 2.42E4 | 2 | 2.5 | 4.84E4 |

Nrf2 Activation by 4-oxo-2-Pentenoic Acid 4-oxo-2-pentenoic acid (Alfa Aesar—reference L02185) was tested in the Nrf2 reporter assay. Different doses of 4-oxo-2-pentenoic acid were applied on AREc32 cells for 24 h and then the luciferase activity was quantified as described above. The cell viability was also measured using a cell Titer-Glo kit (ATP quantification).

As shown in FIG. 3, the 4-oxo-2-pentenoic acid molecule was found to strongly activate Nrf2 in a dose dependent manner. The viability of AREc32 cells was not affected by 4-oxo-2-pentenoic acid at doses lower than 70 μM. The optimal dose of Nrf2 activation was around 40-50 μM. For comparison, FIG. 4 shows that a bacterial fraction of *Bifidobacterium breve* CNCM I-3865 activates Nrf2 in a similar manner.

EXAMPLE 2

The Protection of Neurons Against Oxidative Stress Using 4-oxo-2-pentenoic Acid and Bacterial Fractions The beneficial effect of compounds on cell survival is classically investigated by challenging the cell cultures with neurotoxic insults and measuring the resulting oxidative stress and excitotoxicity over a limited period of time (Aksenova et al., Current Neurovascular Research, 2, 73-89 (2005)). Accordingly, the inventors used a neuron-astrocyte co-culture model to test the potential beneficial effects of 4-oxo-2-pentenoic acid against neurodegeneration induced by oxidative stress. The oxidative stress was induced by hydrogen peroxide and cell survival was compared between cultures treated with 4-oxo-2-pentenoic acid and those left un-treated.

The model consists of primary neurons plated on glass coverslips that face astrocytes seeded on the bottom of a culture dish. The two cellular compartments are separated by paraffin beads, but released compounds (e.g., energy substrates and glutathione precursors) can freely diffuse from one compartment to the other through the culture medium.

Primary cultures of mouse neurons are grown for 12 days in Neurobasal™ medium on 20 mm diameter glass coverslips. Primary cultures of mouse astrocytes are grown for 21 days in astrocytes culture medium in 35 mm diameter dishes. Two hours before initiation of the co-culture, the astrocyte medium is removed and replaced by a fresh neuronal medium. The co-culture is initiated by putting the glass coverslips bearing neurons in the dishes containing astrocyte culture so that neurons face astrocytes. The co-culture is then maintained during 48 hours in the presence or absence of 4-oxo-2-pentenoic acid. At the end of this incubation, the co-culture is challenged with 100 µM hydrogen peroxide for 4 hours or kept non-challenged as a control condition. At the end of the incubation period, neuronal and astrocytic viability are separately assessed by using a MTT assay (2-(4,5-Dimethylthiazol-2-yl)-2,5-diphenyltetrazolium bromide).

The MTT reduction assay was chosen as it is able to monitor cell viability both in neurons and in astrocytes. MTT is a membrane-permeant molecule that is trapped inside viable cells through the action of intracellular enzymes, dehydrogenases and esterases. Inside the cell MTT, which has a yellow colour, can be reduced, mainly by the mitochondrial dehydrogenase enzymes of active cells, into a purple insoluble product called formazan. For detection this purple product is solubilised for colorimetric quantification at 560 nm using a spectrophotometer.

Results were expressed as differences between MTT reduction assay values for 4-oxo-2-pentenoic acid-treated co-cultures and the basal values (no 4-oxo-2-pentenoic acid treatment), normalized as a percentage of their corresponding control (no challenge with hydrogen peroxide). The results are shown in FIG. 5. All tested concentrations, except 10 µM, showed a clear and significant protection. The strongest effect was obtained with 5 µM 4-oxo-2-pentenoic acid.

EXAMPLE 3

Quantification of 4-oxo-2-pentenoic Acid by HPLC-MS/MS

In order to quantify 4-oxo-2-pentenoic acid, a high throughput analytical method involving coupling high performance liquid chromatography with electrospray ionization tandem mass spectrometry (HPLC-ESI-MS/MS) was developed.

Methodology:

4-oxo-2-pentenoic acid standard was purchased from Alfa Aesar (Ward Hill, USA). 4-oxo-2-pentenoic acid was found to be soluble in water to at least 20 mg/ml. 4-oxo-2-pentenoic acid standard compound was solubilised in water at a final stock solution of 10 mg/ml and further diluted in water to build a calibration curve.

HPLC-ESI-MS/MS analyses were carried out on a turbulent flow chromatography (TFC) system (Thermo Fisher, Waltham, Mass.) coupled to a 3200 Q TRAP mass spectrometer (Applied Biosystems). The analytical column used was a Hypersil Gold AQ (3×50 mm, 5 µm) purchased from Thermo Fisher (Waltham, Mass.) running at room temperature and a constant flow rate of 600 µl/min. The mobile phases were constituted with solvent A—water containing 0.05% acetic acid and B—methanol containing 0.05% acetic acid. The gradient program was: 0 min 0% B, held for 40 sec (0-0.67 min) at 0% B, ramping to 50% B in 180 sec (0.67-3.67 min), ramping from 50 to 90% B in 10 sec (3.67-3.83 min), held for 120 sec (5.83 min) at 90% B, before going back to 0% B and held for an additional 300 sec (5.83-10.83 min). The injection volume was 5 µl.

MS data acquisition was realized in electrospray negative ionization mode. MS tuning was performed by infusing a solution of 4-oxo-2-pentenoic acid standard (5 µg/ml in water) at a flow rate of 10 µl/min mixed with a HPLC flow of solvents A and B (80/20, v:v; 0.6 ml/min) using a T-connector. Nitrogen was used for the nebulizer and curtain gases. The interface heater was activated and the block source temperature was maintained at 700° C. with a capillary voltage set at −4.5 kV. Nitrogen was also used as collision gas at a medium pressure selection. MS/MS detection was realized using the selected reaction monitoring (SRM) acquisition mode. The two most intense fragment ions were selected by scanning m/z 113→69 (collision energy of 11 eV), and m/z 113→41 (collision energy of 26 eV), using constant dwell times of 50 ms (total scan time of 110 ms). The declustering potential was set at −29 V. Quantitative analyses were performed using the most intense SRM signal whereas the second transition was used for analyte confirmation based on appropriate area ratio calculated from standard solutions. Data processing was performed using Analyst 1.5.1 software (Applied Biosystems).

Detection of 4-oxo-2-pentenoic Acid in PBS and Water by HPLC-MS/MS:

4-oxo-2-pentenoic acid was solubilised in 1×PBS or water, and the detection by HPLC-MS/MS performed as described in the previous section. The SRM associated with the transition reaction of m/z 113→69 revealed a more intense signal as compared to the SRM associated with the transition m/z 113→41 at a retention time of 1.25 min. Similar retention time for both transitions were observed confirming the validity of the analysis, FIG. 6). The molecule 4-oxo-2-pentenoic acid was successfully detected in both 1×PBS (data not shown) and water (FIG. 6).

Establishment of 4-oxo-2-pentenoic Acid Standard Curve:

In order to quantify precisely the amount of 4-oxo-2-pentenoic acid in bacterial fractions, standard curves were established for 4-oxo-2-pentenoic acid in simple matrices like 1×PBS or HPLC grade water. Commercial 4-oxo-2-pentenoic acid was suspended in 1×PBS and water at different doses. The HPLC-ESI-MS/MS method was then used to quantify the estimated doses of 4-oxo-2-pentenoic acid. Good linearity was observed between the quantity of 4-oxo-2-pentenoic acid (from 0.1 to 25 µg/ml) and the resulting intensities (expressed in cps) both in 1×PBS and HPLC grade water.

Quantification of 4-oxo-2-pentenoic Acid in Bacterial Fractions:

4-oxo-2-pentenoic acid was quantified in the heat treated bacterial preparations from example 1. All samples were diluted in HPLC grade water (3 dilutions/sample) before HPLC-ESI-MS/MS analysis. The results are summarized in table E.

TABLE E

Concentrations of 4-oxo-2-pentenoic acid (µg/ml) in crude and pure bacterial heated preparations (OD 50) from example 1 (6 hours of heating at 90° C.).

| Strain | Strain Code | 4-oxo-2-pentenoic acid (µg/ml) Crude preparation | 4-oxo-2-pentenoic acid (µg/ml) Pure preparation |
|---|---|---|---|
| B. breve | CNCM I-3865 | 95.3 | 126.8 |
| B. breve | ATCC 15700 | 2.1 | 16.4 |
| B. breve | CNCM I-3914 | N.D. | N.D. |

N.D stands for "Not Detectable", below the detection limit of the method.

EXAMPLE 4

The Influence of Heating Temperature and Time on the Production of 4-oxo-2-pentenoic Acid from *Bifidobacterium breve* CNCM I-3865

To characterize the production of 4-oxo-2-pentenoic acid from *Bifidobacterium breve* CNCM I-3865 upon heat treatment a kinetic experiment was performed using various temperatures. The "master stock" of biomass used for this experiment was produced in bioreactors at 37° C. with MRS medium under anaerobic and pH control conditions. After the grow culture (16 h), the culture media was removed and the cells were washed two times with 1×PBS, concentrated to OD 134 (1.5E+10 cfu/ml) in 1×PBS with 10% glycerol then stored at −80° C. in 50 ml aliquots.

A "working biomass" of *Bifidobacterium breve* CNCM I-3865 was then prepared from the biomass master stock as follows: The biomass was washed two times with 1×PBS and adjusted to OD 40 in 1×PBS.

A Temperature Heating Apparatus (THA) was used to investigate the effect of different heating times and temperatures. This system is a small scale version of typical apparatus found in production environments. Steam is used to heat up a holding tube containing cartridges of biomass. Sample temperatures of 90° C., 120° C. and 140° C. were applied for periods up to 60 minutes. 5 ml of each heat-treated biomass was then centrifuged for 10 min at 5000 g and the supernatants were filtered (0.2 µm) and the 4-oxo-2-pentenoic acid content quantified by HPLC-ESI-MS/MS. The amounts of 4-oxo-2-pentenoic acid generated are shown in FIG. 7.

The invention claimed is:

1. A method for the treatment or prevention of cognitive decline comprising administering a non-pharmaceutical composition comprising 4-oxo-2-pentenoic acid to an individual having or at risk of cognitive decline.

2. Method in accordance with claim 1, for use in the treatment or prevention of memory loss.

3. Method in accordance with claim 1 for the treatment or prevention of loss of learning capability.

4. Method in accordance with claim 1, wherein the 4-oxo-2-pentenoic acid is obtained from natural sources.

5. Method in accordance with claim 1, wherein the 4-oxo-2-pentenoic acid is obtainable from *Bifidobacterium breve* CNCM I-3865 or *Bifidobacterium breve* ATCC 15700.

6. Method in accordance with claim 5, wherein the *Bifidobacterium breve* CNCM I-3865 or *Bifidobacterium breve* ATCC 15700 was heat treated at about 60-180° C.

7. Method in accordance with claim 1, wherein the composition comprises 4-oxo-2-pentenoic acid in an amount of at least 1 mg per kg of the composition.

8. Method in accordance with claim 1, wherein the composition is administered in a daily dose corresponding to between 2 µg and 20 mg of 4-oxo-2-pentenoic acid per kg of body weight.

9. Method in accordance with claim 1, wherein the composition is administered orally or enterally.

10. Method in accordance with claim 1, wherein the composition is administered to humans or pets.

11. Method in accordance with claim 1, wherein the composition is administered to adults.

12. Method in accordance with claim 1, wherein the composition is selected from the group consisting of a food composition, a food additive, a nutraceutical, a drink, a nutritional formulation, a tube feeding formulation, a powdered composition to be reconstituted in milk or water, and a pet food composition.

* * * * *